(12) United States Patent
Watanabe et al.

(10) Patent No.: US 7,217,836 B2
(45) Date of Patent: May 15, 2007

(54) PROCESS FOR PRODUCING (METH)ACROLEIN AND/OR (METH)ACRYLIC ACID

(75) Inventors: Seigo Watanabe, Otake (JP); Motomu Oh-Kita, Tokyo (JP); Toshihiro Sato, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 379 days.

(21) Appl. No.: 10/479,228

(22) PCT Filed: May 21, 2002

(86) PCT No.: PCT/JP02/04914

§ 371 (c)(1),
(2), (4) Date: Apr. 20, 2004

(87) PCT Pub. No.: WO02/098827

PCT Pub. Date: Dec. 12, 2002

(65) Prior Publication Data

US 2004/0171874 A1    Sep. 2, 2004

(30) Foreign Application Priority Data

May 30, 2001 (JP) ............................. 2001-162454
Jun. 27, 2001 (JP) ............................. 2001-194903

(51) Int. Cl.
*C07C 51/235* (2006.01)
*C07C 51/16* (2006.01)
*C07C 45/00* (2006.01)

(52) U.S. Cl. ..................... 562/534; 562/537; 568/477

(58) Field of Classification Search ................ 562/534, 562/537; 568/477; 502/38
See application file for complete search history.

(56) References Cited

U.S. PATENT DOCUMENTS 5,276,178 A * 1/1994 Onodera et al. ............ 562/537
6,346,646 B1 * 2/2002 Watanabe et al. .......... 562/534

FOREIGN PATENT DOCUMENTS

| EP | 987057 | 3/2000 |
| EP | 1055662 | 11/2000 |
| JP | 2001-55355 | 2/2001 |

OTHER PUBLICATIONS

U.S. Appl. No. 10/479,228, filed Dec. 1, 2003, Watanabe et al.

* cited by examiner

*Primary Examiner*—Samuel A Barts
*Assistant Examiner*—Lalitha Nagubandi
(74) *Attorney, Agent, or Firm*—Oblon, Spivak, McClelland, Maier & Neustadt, P.C.

(57) ABSTRACT

A method for producing (meth)acrolein and/or (meth)acrylic acid by subjecting isobutylene and the like or propylene to a vapor-phase catalytic oxidation with molecular oxygen in the presence of a solid oxidation catalyst in a tubular type of fixed bed reactor, wherein a temperature of a hot-spot zone is sufficiently controlled and (meth)acrolein and (meth)acrylic acid are produced with a high yield.

A method for producing (meth)acrolein and/or (meth)acrylic acid by passing a raw material gas comprising isobutylene and the like or propylene and oxygen through a catalyst layer in a tubular type of fixed bed reactor which is filled with a solid oxidation catalyst, which includes passing a gas containing isobutylene and the like or propylene in a concentration lower than that of the raw material gas, and oxygen through the catalyst layer for a period of one hour or more prior to passing the raw material gas through the catalyst layer.

6 Claims, No Drawings

US 7,217,836 B2

PROCESS FOR PRODUCING (METH)ACROLEIN AND/OR (METH)ACRYLIC ACID

TECHNICAL FIELD

The present invention relates to a method of producing methacrolein and/or methacrylic acid, which comprises subjecting isobutylene and/or tertiary butanol to a vapor-phase catalytic oxidation with molecular oxygen in the presence of a solid oxidation catalyst by employing a tubular type of fixed bed reactor.

The present invention also relates to a method of producing acrolein and/or acrylic acid, which comprises subjecting propylene to vapor-phase catalytic oxidation with molecular oxygen in the presence of a solid oxidation catalyst by employing a tubular type of fixed bed reactor.

BACKGROUND ART

With respect to a catalyst which is used when isobutylene and/or tertiary butanol are subjected to a vapor-phase catalytic oxidation so as to produce methacrolein and/or methacrylic acid, and a catalyst which is used when propylene is subjected to a vapor-phase catalytic oxidation so as to produce acrolein and/or acrylic acid, a number of proposals have been made. These proposals relate primarily to elements constituting the catalyst and to the ratios thereof.

The above vapor-phase catalytic oxidation is an exothermic reaction, which causes thermal storage in a catalyst layer. A high temperature local zone which results from the thermal storage is referred to as a "hot-spot". An excessive high temperature of this zone causes excessive oxidation, whereby the yield of an object product is decreased. Therefore, in the industrial operation of the above oxidation, the inhibition of the temperature of a hot-spot is a serious problem. In particular, when concentrations of isobutylene and/or tertiary butanol (which may be referred to as "isobutylene and the like") or propylene in a raw material gas are increased so as to increase the productivity, the temperature of a hot-spot tends to be elevated, and therefore, reaction conditions therefor are actually subjected to large constraints.

Therefore, in order to industrially produce (meth)acrolein and/or (meth)acrylic acid with a high yield, it is very important to control the temperature of a hot-spot zone. Furthermore, in particular, when a solid oxidation catalyst including molybdenum is used, it is important to prevent a generation of the hot-spot because the molybdenum component is apt to easily sublimate.

Additionally, the term "(meth)acrolein" means "methacrolein and/or acrolein", and the term "(meth)acrylic acid" means "methacrylic acid and/or acrylic acid".

Heretofore, several methods of controlling the temperature of a hot-spot zone have been proposed. For example, JP-A-3-176440 discloses a method which comprises filling a reactor with a plural kinds of catalysts, which are different from each other on activities and have been prepared by varying their compositions, so that the activities are increasingly enhanced from the inlet side of a raw material gas toward the outlet side thereof, and passing a raw material gas including oxygen, isobutylene and the like through the catalysts layer. JP-A-55-113730 discloses a method which comprises filling a reactor with a plural kinds of catalysts, which are different from each other on activities and have been prepared by varying their compositions, so that the activities are increasingly enhanced from the inlet side of a raw material gas toward the outlet side thereof, and passing a raw material gas including oxygen and propylene through the catalysts layer. JP-A-8-92147 discloses a method which comprises controlling a flow of a heating medium so that a temperature of a heating medium bath be elevated by 2° C. to 10° C. between the inlet port of a multi-tubular type of fixed bed reactor having the heating medium bath and the outlet port thereof, when propylene is subjected to a vapor-phase oxidation into acrolein by using the reactor.

Each of these methods is the one in which the rate of reaction per unit volume at an inlet side for a raw material gas in a catalyst layer within a reactor is lowered so as to control a calorific value of reaction per unit volume, so that the temperature of a hot-spot zone can be lowered.

Furthermore, JP-A-2001-55355 discloses a method of producing an unsaturated nitrile and/or an unsaturated carboxylic acid, which comprises subjecting a hydrocarbon to a-vapor-phase catalytic oxidation in the presence of a compound metal-oxide catalyst including, as an essential ingredient(s), molybdenum, vanadium, and at least one element selected from the group consisting of tellurium and antimony, wherein the temperature is elevated in an atmosphere in which oxygen and/or a combustible gas are substantially included, until the temperature of the catalyst layer reaches a temperature at which a reaction can be initiated. Besides, in comparative example of the specification thereof, a method of elevating the temperature in an atmosphere of air is also disclosed.

DISCLOSURE OF INVENTION

However, there has been a problem that the temperature of a hot-spot zone can not be sufficiently controlled by merely these methods and the yield of each of (meth)acrolein and (meth)acrylic acid is low.

It is an object of the present invention to provide a method for producing (meth)acrolein and/or (meth)acrylic acid by subjecting isobutylene and the like or propylene to a vapor-phase catalytic oxidation with molecular oxygen in the presence of a solid oxidation catalyst in a tubular type of fixed bed reactor, whereby a temperature of a hot-spot zone is sufficiently controlled and (meth)acrolein and (meth)acrylic acid are produced with a high yield.

The present invention provides a method for producing (meth)acrolein and/or (meth)acrylic acid by passing a raw material gas comprising isobutylene and the like or propylene and oxygen through a catalyst layer in a tubular type of fixed bed reactor which is filled with a solid oxidation catalyst, which comprises passing a gas comprising isobutylene and the like or propylene in a concentration lower than that of said raw material gas, and oxygen through said catalyst layer for a period of one hour or more prior to passing said raw material gas through said catalyst layer.

In particular, the present invention also provides a method for producing (meth)acrolein and/or (meth)acrylic acid, which comprises:

filling a tubular type of fixed bed reactor with a solid oxidation catalyst;

elevating a temperature of the resultant catalyst layer to a range of 250° C. to 400° C. while passing a gas including oxygen, nitrogen, water vapor and 0 to 0.5% by volume of isobutylene and the like or propylene through said catalyst layer; and passing a gas including 1 to 3.8% by volume of isobutylene and the like or propylene, 7 to 16% by volume of oxygen and 5 to 50% by volume of water vapor through said catalyst layer at a temperature of 250° C. to 400° C. for a period of one hour or more; and thereafter passing a raw material gas including 4 to 9% by volume of isobutylene and the like or propylene, 7 to 16% by volume of oxygen and 5 to 50% by volume of water vapor through said catalyst layer at a temperature of 250° C. to 400° C.

In the present invention, a reaction for synthesizing (meth)acrolein and/or (meth)acrylic acid is carried out by using a tubular type of fixed bed reactor. The tubular type of fixed bed reactor is industrially and preferably, but not in particular limited to, a multi-tubular type of fixed bed reactor which is provided with several thousands to several tens thousand of reaction tubes having an inner diameter of 10 to 40 mm. Furthermore, the tubular type of fixed bed reactor is preferably the one as provided with a heating medium bath. The heating medium is not in particular limited, and includes salt melts such as potassium nitrate and sodium nitrite.

In the present invention, a solid oxidation catalyst to be used is not in particular limited, provided that the catalyst is a solid catalyst for this oxidation reaction, and a compound oxide including molybdenum which has been conventionally known and the like can be used therefor. For a reaction wherein isobutylene and the like are used as raw materials, a compound oxide as represented by the following formula (1):

$$Mo_aBi_bFe_cA_dX_eY_fZ_gO_h \quad (1)$$

wherein Mo, Bi, Fe and O represent molybdenum, bismuth, iron and oxygen, respectively; A represents nickel and/or cobalt; X represents at least one element selected from the group consisting of magnesium, zinc, chromium, manganese, tin and lead; Y represents at least one element selected from the group consisting of phosphorus, boron, sulfur, tellurium, silicon, germanium, cerium, niobium, titanium, zirconium, tungsten and antimony; Z represents at least one element selected from the group consisting of potassium, sodium, rubidium, cesium and thallium; and each of a, b, c, d, e, f, g and h represents an atomic ratio of each element, wherein $0.1 \leq b \leq 5$, $0.1 \leq c \leq 5$, $1 \leq d \leq 12$, $0 \leq e \leq 10$, $0 \leq f \leq 10$ and $0.01 \leq g \leq 3$ when $a=12$, and h means an atomic ratio of oxygen necessary to satisfy the atomic valence of each of said elements, is preferred as a catalyst. A particularly preferred atomic ratio of each element is $0.2 \leq b \leq 3$, $0.5 \leq c \leq 4$, $2 \leq d \leq 10$ and $0.1 \leq g \leq 2$ when $a=12$.

Besides, for a reaction wherein propylene is used as a raw material, a compound oxide as represented by the following formula (2):

$$Mo_{a'}Bi_{b'}Fe_{c'}A'_{d'}X'_{e'}Y'_{f'}Z'_{g'}Si_{h'}O_i \quad (2)$$

wherein Mo, Bi, Fe, Si and O represent molybdenum, bismuth, iron, silicon and oxygen, respectively; A' represents nickel and/or cobalt; X' represents at least one element selected from the group consisting of magnesium, zinc, chromium, manganese, tin, strontium, barium, copper, silver and lead; Y' represents at least one element selected from the group consisting of phosphorus, boron, sulfur, tellurium, aluminum, gallium, germanium, indium, lanthanum, cerium, niobium, tantalum, titanium, zirconium, tungsten and antimony; Z' represents at least one element selected from the group consisting of potassium, sodium, rubidium, cesium and thallium; each of a', b', c', d', e', f', g', h' and i represents an atomic ratio of each element, wherein $0.01 \leq b' \leq 5$, $0.01 \leq c' \leq 5$, $1 \leq d' \leq 12$, $0 \leq e' \leq 10$, $0 \leq f' \leq 10$, $0.001 \leq g' \leq 3$ and $0 \leq h' \leq 20$ when $a'=12$, and i means an atomic ratio of oxygen necessary to satisfy the atomic valence of each of said elements, is preferred as a catalyst. A particularly preferred atomic ratio of each element is $0.1 \leq b' \leq 3$, $0.1 \leq c' \leq 4$, $2 \leq d' \leq 10$ and $0.005 \leq g' \leq 2$ when $a'=12$.

A method of preparing the catalyst to be used in the present invention is not in particular limited, and various methods as conventionally well known can be used, provided that components do not cause remarkable maldistribution.

Raw materials as used for preparing the catalyst are not in particular limited, and a nitrate, a carbonate, an acetate, an ammonium salt, an oxide and a halide and the like of each element can be used in combination to each other. For example, as a molybdenum raw material, ammonium paramolybdate, molybdenum trioxide, molybdenum chloride or the like can be used.

The catalyst used in the present invention can be used with no carrier, while the catalyst can be used in the form of a supported catalyst which is supported on an inactive carrier such as silica, alumina, a silica-alumina, or silicon-carbide, or in the form of a catalyst diluted with such an inactive carrier.

In the present invention, the term "a catalyst layer" means a space zone in a reaction tube of a tubular type of fixed bed reactor, which includes at least a catalyst; that is to say, not only a space which is filled with merely a catalyst but also a space in which a catalyst is diluted with an inactive carrier or the like are referred to as "a catalyst layer". However, a space at each end as filled with nothing, or a space as filled with merely an inactive carrier or the like are not referred to as "a catalyst layer", because no catalyst is substantially included therein.

A reaction for synthesizing (meth)acrolein and/or (meth)acrylic acid, which comprises subjecting isobutylene and the like or propylene to vapor-phase catalytic oxidation with molecular oxygen in the presence of a solid oxidation catalyst by employing a tubular type of fixed bed reactor, which is simply referred to as "an oxidation reaction", is preferably carried out at a reaction temperature in the range of 250° C. to 400° C. However, when a raw material gas including, for example, 4 to 9% by volume of isobutylene and the like or propylene, 7 to 16% by volume of oxygen, and 5 to 50% by volume of water vapor, which is simply referred to as "a raw material gas", is passed from the initiation of reaction through a catalyst layer whose temperature is maintained at a reaction temperature of about 250° C. to about 400° C., a hot-spot having a high maximum temperature tends to be formed near a raw material gas inlet port of the catalyst layer.

The present inventor has made extensive studies to solve this problem. As a result, it has been found that according to a method for producing (meth)acrolein and/or (meth)acrylic acid by passing a raw material gas comprising isobutylene and the like or propylene, and oxygen through a catalyst layer in a tubular type of fixed bed reactor which is filled with a solid oxidation catalyst, which comprises passing a gas comprising isobutylene and the like or propylene in a concentration lower than that of said raw material gas, and oxygen through said catalyst layer for a period of one hour or more prior to passing said raw material gas through said catalyst layer, when an oxidation reaction is carried out under usual reaction conditions, a temperature of a hot-spot zone can be sufficiently controlled, and as a result, (meth) acrolein and/or (meth)acrylic acid can be produced with a high yield.

In particular, according to a method which comprises elevating a temperature of the catalyst layer to a temperature of 250° C. to 400° C. while passing a gas comprising oxygen, nitrogen, water vapor and 0 to 0.5% by volume of isobutylene and the like or propylene through said catalyst layer; and passing a gas comprising 1 to 3.8% by volume of isobutylene and the like or propylene, 7 to 16% by volume of oxygen and 5 to 50% by volume of water vapor at a temperature of 250° C. to 400° C. through said catalyst layer for a period of one hour or more, prior to passing the above raw material gas through the catalyst layer, when an oxidation reaction is carried out under usual reaction conditions, that is, at a reaction temperature of 250° C. to 400° C. using the above raw material gas, the temperature of the hot-spot zone can be in particular sufficiently controlled.

A temperature of the catalyst layer before elevating the temperature of the catalyst layer to the range of 250° C. to 400° C., that is, the temperature at which the temperature-elevation is started is not in particular limited, but is preferably in the range of 10° C. to 240° C. Furthermore, a temperature-elevation rate also is not in particular limited, but is preferably in the range of 10 to 500° C./hour, particularly 20 to 400° C./hour.

A passing gas which is passed for elevating the temperature of the catalyst layer to the range of 250° C. to 400° C. is a gas comprising isobutylene and the like or propylene, and oxygen, preferably comprising 0 to 0.5% by volume of isobutylene and the like or propylene, oxygen, nitrogen and water vapor. The concentrations of oxygen, nitrogen and water vapor in this gas are not in particular limited, but preferably, oxygen is in the range of 1 to 21% by volume, nitrogen is in the range of 29 to 98.5% by volume, and water vapor is in the range of 0.5 to 50% by volume. Besides, isobutylene and the like or propylene is in the range of 0 to 0.5% by volume, preferably 0 to 0.3% by volume, and in particular preferably 0 to 0.1% by volume. When a gas comprising isobutylene and the like or propylene in an amount exceeding 0.5% by volume is passed with the temperature of the catalyst layer lower than 250° C., compounds having a relatively high boiling point which is produced on the catalyst may poison active sites of the catalyst. Incidentally, the wording "the concentration of isobutylene and the like" means the sum of the concentration of each of isobutylene and tertiary butanol. This passing gas can include other gases in addition to oxygen, nitrogen, water vapor, and isobutylene and the like or propylene. As such other gases, for example, an inert gas such as carbon dioxide, lower saturated aldehyde, and ketone and the like can be enumerated. However, when an organic compound such as lower saturated aldehyde is included, the sum of the concentration of each of isobutylene and the like or propylene and other organic compounds is preferably 0.5% by volume or less. When the temperature of the catalyst layer is elevated, the flow rate of the passing gas is not particularly limited; however, such a flow rate to provide a space velocity of 100 to 2000 hours$^{-1}$ is preferred. In this case, the internal pressure of the reactor is usually from atmospheric pressure to several atmospheric pressure.

The above gas which is passed through the catalyst layer after elevating the temperature of the catalyst layer is the one including 1 to 3.8% by volume of isobutylene and the like or propylene, 7 to 16% by volume of oxygen and 5 to 50% by volume of water vapor. The concentration of isobutylene and the like or propylene is preferably in the range of 1 to 3% by volume, and in particular preferably 1 to 2.5% by volume; the concentration of oxygen is preferably in the range of 7.5 to 14% by volume, and in particular preferably 8 to 12% by volume; and the concentration of water vapor is preferably in the range of 2 to 40% by volume, and in particular preferably 4 to 30% by volume. When this gas is passed, the temperature of the gas is in the range of 250 to 400° C. Furthermore, a period of time during which the gas is passed is one hour or more, preferably 1.5 to 100 hours, and in particular preferably 2 to 50 hours. This gas can include other gases in addition to oxygen, water vapor, and isobutylene and the like or propylene. As such other gases, for example, nitrogen, carbon dioxide, lower saturated aldehyde, and ketone and the like can be enumerated. The flow rate of the gas which is passed after elevating the temperature of the catalyst layer is not particularly limited; however, such a flow rate to provide a space velocity of 100 to 3000 hour$^{-1}$ is preferred. In this case, the internal pressure of the reactor is usually from atmospheric pressure to several atmospheric pressure. When the gas is passed, a hot-spot zone having a low maximum temperature is formed over a large area.

Thereafter, when an oxidation reaction is carried out under the above reaction conditions, that is, at a reaction temperature of 250 to 400° C. using a raw material gas including 4 to 9% by volume of isobutylene and the like or propylene, the maximum temperature of the hot-spot zone is in particular restrained. As a result, sequential oxidation on the hot-spot zone is in particular restrained, whereby (meth)acrolein and (meth)acrylic acid can be produced with a high yield. The flow rate of the raw material gas is not particularly limited; however, such a flow rate to provide a space velocity of 300 to 3000 hour$^{-1}$, particularly 500 to 2000 hour$^{-1}$, is preferred. The reaction temperature for the oxidation reaction is preferably in the range of 250° C. to 400° C., and in particular preferably in the range of 280° C. to 380° C. Besides, the reaction pressure is usually from atmospheric pressure to several atmospheric pressure.

When the present invention is carried out, it is economically advantageous to use air as an oxygen source for the raw material gas, the gas which is passed on elevating the temperature of a catalyst layer, and the gas which is passed after elevating the catalyst layer temperature.

BEST MODE FOR CARRYING OUT THE INVENTION

Examples will be enumerated hereinafter to more particularly explain the present invention. Incidentally, the unit "part(s)" in Examples and Comparative Examples means "part(s) by mass". The composition of a catalyst was calculated from the amounts of charged raw materials of catalyst components. As a heating medium for a reactor, a salt melt comprising 50% by mass of potassium nitrate and 50% by mass of sodium nitrite was used. A hot-spot was detected from ΔT of a catalyst layer (i.e., the temperature of the catalyst layer minus the temperature of a heating medium bath).

A temperature within the catalyst layer was measured by using a thermocouple inserted in a protective tube which was located at a center of a cross-section perpendicular to a tube axial direction of a reaction tube. Additionally, the inside of the protective tube was separated from a system of reaction, while the position of temperature measurement could be shifted by adjusting the length of the thermocouple as inserted thereinto.

The analyses of a raw material gas and a product gas of reaction were carried out by means of gas chromatography.

In addition, the rate of reaction of isobutylene and the like or propylene, the selectivity factors of produced (meth)acrolein and (meth)acrylic acid, and the yield of (meth)acrolein and (meth)acrylic acid are defined as follows, respectively:

Rate of reaction of isobutylene and the like or propylene (%)=(B/A)×100;
Selectivity factor of (meth)acrolein (%)=(C/B)×100;
Selectivity factor of (meth)acrylic acid (%)=(D/B)×100; and
Yield of (meth)acrolein and (meth)acrylic acid (%)={(C+D)/A)}×100, wherein A represents the number of moles of fed isobutylene and the like or propylene; B represents the number of moles of reacted isobutylene and the like or propylene; C represents the number of moles of produced (meth)acrolein; and D represents the number of moles of produced (meth)acrylic acid.

EXAMPLE 1

To 1000 parts of water, 500 parts of ammonium paramolybdate, 18.5 parts of ammonium paratungstate, 18.4 parts of cesium nitrate and 354.5 parts of silicasol of 20% by mass were added, heated and agitated (Liquid A). Aside from this, to 850 parts of water, 250 parts of nitric acid of 60% by mass were added and homogenized, and then 57.2 parts of bismuth nitrate was added thereto and dissolved. To the mixture, 238.4 parts of ferric nitrate, 4.7 parts of chromium(III) nitrate, 411.8 parts of nickel(II) nitrate and 60.5 parts of magnesium nitrate were sequentially added, and dissolved (Liquid B). Liquid B was added to Liquid A into a slurry, and then 34.4 parts of antimony trioxide were added thereto and heated and agitated, so that most of water was evaporated. The resultant caked matter was dried at a temperature of 120° C., and then calcined at a temperature of 500° C. for a period of six hours. To 100 parts of the resultant calcined product, 2 parts of graphite were added, which were then formed into rings having an outer diameter of 5 mm, an inner diameter of 2 mm and a length of 5 mm by using a tablet forming machine, whereby Catalyst 1 was obtained. The elementary composition of Catalyst 1 comprised $Mo_{12}Bi_{0.5}Fe_{2.5}Ni_6Mg_1Cr_{0.05}W_{0.3}Sb_1Si_5Cs_{0.4}$, except oxygen.

The temperature of a heating medium bath of a tubular type of fixed bed steel reactor having an inner diameter of 25.4 mm with the heating medium bath was set to a temperature of 180° C., and an inlet side for raw material gas was filled with a mixture of 620 ml of Catalyst 1 and 130 ml of a spherical alumina having an outer diameter of 5 mm, while an outlet side was filled with 750 ml of Catalyst 1, wherein the length of a catalyst layer was 3005 mm.

The heating medium bath temperature was elevated to a temperature of 340° C. at a rate of 50° C./hour, while a gas comprising 9% by volume of oxygen, 10% by volume of water vapor and 81% by volume of nitrogen was passed through this catalyst layer at a space velocity of 240 hour$^{-1}$.

Then, with the heating medium bath temperature maintained at a temperature of 340° C., a gas (i. e., a passing gas after elevating the temperature) comprising 2% by volume of isobutylene, 8% by volume of oxygen, 15% by volume of water vapor and 75% by volume of nitrogen was passed through the catalyst layer at a space velocity of 1000 hours$^{-1}$ for a period of three hours.

Subsequently, with the heating medium bath temperature maintained at a temperature of 340° C., a raw material gas comprising 5% by volume of isobutylene, 12% by volume of oxygen, 10% by volume of water vapor and 73% by volume of nitrogen was passed through the catalyst layer at a reaction temperature (i. e., a heating medium bath temperature) of 340° C. at a space velocity of 1000 hour$^{-1}$.

When the temperatures of the catalyst layer were measured at this time, a hot spot having a maximum temperature was observed at a site located 500 mm apart from the end of the inlet side for the raw material gas, wherein ΔT at the maximum temperature was 33° C. In addition, the rate of reaction of isobutylene was 95.5%, the selectivity factor of methacrolein was 85.7%, the selectivity factor of methacrylic acid was 3.6%, and the yield of methacrolein and methacrylic acid was 85.3%.

EXAMPLE 2

An oxidation reaction was carried out in a similar manner to that in Example 1, except that the composition of a passing gas after elevating the temperature was changed to the one comprising 2.6% by volume of isobutylene, 8% by volume of oxygen, 15% by volume of water vapor and 74.4% by volume of nitrogen. As a result, a hot spot having a maximum temperature was observed at a site located 470 mm apart from the end of the raw material gas inlet side of a catalyst layer, wherein ΔT at the maximum temperature was 35° C. In addition, the rate of reaction of isobutylene was 95.6%, the selectivity factor of methacrolein was 85.4%, the selectivity factor of methacrylic acid was 3.6%, and the yield of methacrolein and methacrylic acid was 85.1%.

EXAMPLE 3

An oxidation reaction was carried out in a similar manner to that in Example 1, except that the time for passing the passing gas after elevating the temperature was changed to 1.5 hours. As a result, a hot spot having a maximum temperature was observed at a site located 470 mm apart from the end of the raw material gas inlet side of a catalyst layer, wherein ΔT at the maximum temperature was 35° C. In addition, the rate of reaction of isobutylene was 95.7%, the selectivity factor of methacrolein was 85.3%, the selectivity factor of methacrylic acid was 3.6%, and the yield of methacrolein and methacrylic acid was 85.1%.

COMPARATIVE EXAMPLE 1

An oxidation reaction was carried out in a similar manner to that in Example 1, except that the temperature of a heating medium bath was elevated to 340° C. without passing the passing gas after elevating the temperature, and except that thereafter a raw material gas was immediately passed through the catalyst layer. As a result, a hot spot having a maximum temperature was observed at a site located 400 mm apart from the end of the raw material gas inlet side of the catalyst layer, wherein ΔT at the maximum temperature was 45° C. In addition, the rate of reaction of isobutylene was 94.3%, the selectivity factor of methacrolein was 83.1%, the selectivity factor of methacrylic acid was 3.7%, and the yield of methacrolein and methacrylic acid was 81.9%.

COMPARATIVE EXAMPLE 2

An oxidation reaction was carried out in a similar manner to that in Example 1, except that the time for passing the passing gas after elevating the temperature was changed to ten minutes. As a result, a hot spot having a maximum temperature was observed at a site located 400 mm apart from the end of the raw material gas inlet side of the catalyst layer, wherein ΔT at the maximum temperature was 44° C.

In addition, the rate of reaction of isobutylene was 94.4%, the selectivity factor of methacrolein was 83.2%, the selectivity factor of methacrylic acid was 3.7%, and the yield of methacrolein and methacrylic acid was 82.0%.

COMPARATIVE EXAMPLE 3

An oxidation reaction was carried out in a similar manner to that in Example 1, except that the composition of the passing gas after elevating the temperature was changed to the one comprising 4.5% by volume of isobutylene, 12% by volume of oxygen, 10% by volume of water vapor and 73.5% by volume of nitrogen. As a result, a hot spot having a maximum temperature was observed at a site located 400 mm apart from the end of the raw material gas inlet side of a catalyst layer, wherein $\Delta T$ at this maximum temperature was 45° C. In addition, the rate of reaction of isobutylene was 94.3%, the selectivity factor of methacrolein was 83.1%, the selectivity factor of methacrylic acid was 3.7%, and the yield of methacrolein and methacrylic acid was 81.9%.

COMPARATIVE EXAMPLE 4

An oxidation reaction was carried out in a similar manner to that in Example 1, except that the composition of the passing gas after elevating the temperature was changed to the one comprising 0.6% by volume of isobutylene, 8% by volume of oxygen, 15% by volume of water vapor and 76.4% by volume of nitrogen. As a result, a hot spot having a maximum temperature was observed at a site located 400 mm apart from the end of the raw material gas inlet side of the catalyst layer, wherein $\Delta T$ at this maximum temperature was 44° C. In addition, the rate of reaction of isobutylene was 94.4%, the selectivity factor of methacrolein was 83.2%, the selectivity factor of methacrylic acid was 3.7%, and the yield of methacrolein and methacrylic acid was 82.0%.

COMPARATIVE EXAMPLE 5

An oxidation reaction was carried out in a similar manner to that in Example 1, except that the composition of the gas as passed when the temperature of a heating medium bath was elevated to 340° C. was changed to the one comprising 2% by volume of isobutylene, 8% by volume of oxygen, 15% by volume of water vapor and 75% by volume of nitrogen. As a result, a hot spot having a maximum temperature was observed at a site located 550 mm apart from the end of the raw material gas inlet side of a catalyst layer, wherein $\Delta T$ at this maximum temperature was 31° C. In addition, the rate of reaction of isobutylene was 92.2%, the selectivity factor of methacrolein was 85.8%, the selectivity factor of methacrylic acid was 3.4%, and the yield of methacrolein and methacrylic acid was 82.2%. From the results, it is considered that the catalyst was poisoned when the temperature thereof was elevated, because $\Delta T$ at the hot spot was decreased as compared to the one in Example 1 while the rate of reaction of isobutylene also was decreased.

EXAMPLE 4

To 400 parts of water, 42 parts of 60% nitric acid were added to form a homogeneous solution, to which 68.7 parts of bismuth nitrate was then added and dissolved. 102.9 parts of nickel nitrate and 24.1 parts of antimony trioxide were sequentially added thereto. To this mixed liquid, 165 parts of 28% aqueous ammonia was added so as to obtain a white precipitate and a blue supernatant. These were heated and agitated so as to evaporate most of water. The resultant slurry was dried at a temperature of 120° C. for a period of 16 hours, and then heat-treated at a temperature of 750° C. for a period of two hours, and pulverized so as to obtain fine powder of a bismuth-nickel-antimony compound.

To 1000 parts of water, 500 parts of ammonium paramolybdate, 12.3 parts of ammonium paratungstate and 23.0 parts of cesium nitrate were added, heated and agitated (Liquid C). Aside from this, to 700 parts of water, 230.8 parts of ferric nitrate, 418.9 parts of cobalt nitrate and 60.5 parts of magnesium nitrate were sequentially added and dissolved (Liquid D). Liquid D was added to Liquid C to form a slurry, to which 425.5 parts of 20% silica-sol and the above-mentioned bismuth-nickel-antimony compound fine powder were then added, heated and agitated, so that most of water was evaporated. The resultant caked matter was dried at a temperature of 130° C., and then calcined at a temperature of 300° C. in an air atmosphere for a period of one hour, and pulverized. To 100 parts of the resultant pulverized product, 2 parts of graphite were added and mixed. The mixture were formed into rings having an outer diameter of 5 mm, an inner diameter of 2 mm and a length of 3 mm by using a tablet forming machine. This formed tablet product was calcined at a temperature of 520° C. for a period of three hours while air was passed, whereby Catalyst 2 was obtained. The elementary composition of Catalyst 2 comprised $Mo_{12}W_{0.2}Bi_{0.6}Fe_{2.4}Sb_{0.7}Ni_{1.5}Co_{6.1}Mg_{1.0}Cs_{0.5}Si_{6.0}$ by an atomic ratio except oxygen.

The temperature of a heating medium bath of a tubular type of fixed bed steel reactor having an inner diameter of 25.4 mm as provided with the heating medium bath was set to a temperature of 180° C., and the inlet side for raw material gas was filled with a mixture of 620 ml of Catalyst 2 and 130 ml of a spherical alumina having an outer diameter of 5 mm, while the outlet side was filled with 750 ml of Catalyst 2, wherein the length of a catalyst layer was 3005 mm.

The heating medium bath temperature was elevated to a temperature of 340° C. at a rate of 50° C./hour, while a gas comprising 9% by volume of oxygen, 10% by volume of water vapor and 81% by volume of nitrogen was passed through this catalyst layer at a space velocity of 240 hour$^{-1}$.

Then, with the heating medium bath temperature maintained at a temperature of 340° C., a gas comprising 2% by volume of tertiary butanol, 8% by volume of oxygen, 15% by volume of water vapor and 75% by volume of nitrogen was passed through the catalyst layer at a space velocity of 1000 hour$^{-1}$ for a period of three hours.

Subsequently, with the heating medium bath temperature maintained at a temperature of 340° C., a raw material gas comprising 5% by volume of tertiary butanol, 12% by volume of oxygen, 10% by volume of water vapor and 73% by volume of nitrogen was passed through the catalyst layer at a reaction temperature (i. e., a heating medium bath temperature) of 340° C. at a space velocity of 1000 hour$^{-1}$. When the temperatures of the catalyst layer were measured at this time, a hot spot having a maximum temperature was observed at a site located 550 mm apart from the end of the inlet side for the raw material gas, wherein $\Delta T$ at the maximum temperature was 32° C. In addition, the rate of reaction of tertiary butanol was 100.0%, the selectivity factor of methacrolein was 84.0%, the selectivity factor of methacrylic acid was 3.2%, and the yield of methacrolein and methacrylic acid was 87.2%.

COMPARATIVE EXAMPLE 6

An oxidation reaction was carried out in a similar manner to that in Example 4, except that the temperature of a heating medium bath was elevated to 340° C. without passing the passing gas after elevating the temperature, and except that thereafter a raw material gas was immediately passed through the catalyst layer. As a result, a hot spot having a maximum temperature was observed at a site located 450 mm apart from the end of the raw material gas inlet side of the catalyst layer, wherein ΔT at the maximum temperature was 44° C. In addition, the rate of reaction of tertiary butanol was 100.0%, the selectivity factor of methacrolein was 81.7%, the selectivity factor of methacrylic acid was 3.3%, and the yield of methacrolein and methacrylic acid was 85.0%.

EXAMPLE 5

To 1000 parts of water, 500 parts of ammonium paramolybdate, 6.2 parts of ammonium paratungstate, 1.4 parts of potassium nitrate and 212.7 parts of silicasol of 20% by mass were added, heated and agitated (Liquid A). Aside from this, to 850 parts of water, 50 parts of nitric acid of 60% by mass were added and homogenized, and then 103.0 parts of bismuth nitrate were added thereto and dissolved. To the mixture, 114.4 parts of ferric nitrate, 274.7 parts of cobalt nitrate, 34.3 parts of nickel(II) nitrate, 7.0 parts of zinc nitrate and 30.3 parts of magnesium nitrate were sequentially added and dissolved (Liquid B). Liquid B was added to Liquid A to form a slurry, and then 10.3 parts of antimony trioxide were added thereto and heated and agitated, so that most of water was evaporated. The resultant caked matter was dried at a temperature of 120° C., and then calcined at a temperature of 500° C. for a period of four hours. To 100 parts of the resultant calcined product, 2 parts of graphite were added, which were then formed into rings having an outer diameter of 4 mm, an inner diameter of 2 mm and a length of 4 mm by using a tablet forming machine, whereby Catalyst 1 was obtained. The elementary composition of Catalyst 1 comprised $Mo_{12}W_{0.1}Bi_{0.9}Fe_{1.2}Co_4Ni_{0.5}Zn_{0.1}Mg_{0.5}Sb_{0.3}K_{0.06}Si_3$, except oxygen.

The temperature of a heating medium bath of a tubular type of fixed bed steel reactor having an inner diameter of 25.4 mm as provided with the heating medium bath was set to a temperature of 180° C., and the inlet side for raw material gas was filled with a mixture of 620 ml of Catalyst 1 and 130 ml of a spherical alumina having an outer diameter of 5 mm, while the outlet side was filled with 750 ml of Catalyst 1, wherein the length of a catalyst layer was 3005 mm.

The heating medium bath temperature was elevated to a temperature of 310° C. at a rate of 50° C./hour, while a gas comprising 9% by volume of oxygen, 10% by volume of water vapor and 81% by volume of nitrogen was passed through this catalyst layer at a space velocity of 240 hour$^{-1}$.

Then, with the heating medium bath temperature maintained at a temperature of 310° C., a gas (i. e., a passing gas after elevating the temperature) comprising 2% by volume of propylene, 8% by volume of oxygen, 15% by volume of water vapor and 75% by volume of nitrogen was passed through the catalyst layer at a space velocity of 1000 hour$^{-1}$ for a period of three hours.

Subsequently, with the heating medium bath temperature maintained at a temperature of 310° C., a raw material gas comprising 5% by volume of propylene, 12% by volume of oxygen, 10% by volume of water vapor and 73% by volume of nitrogen was passed through the catalyst layer at a reaction temperature (i. e., a heating medium bath temperature) of 340° C. at a space velocity of 1000 hour$^{-1}$. When the temperatures of the catalyst layer were measured at this time, a hot spot having a maximum temperature was observed at a site located 500 mm apart from the end of the inlet side for the raw material gas, wherein ΔT at the maximum temperature was 29° C. In addition, the rate of reaction of propylene was 98.5%, the selectivity factor of acrolein was 88.3%, the selectivity factor of acrylic acid was 5.8%, and the yield of acrolein and acrylic acid was 92.7%.

EXAMPLE 6

An oxidation reaction was carried out in a similar manner to that in Example 1, except that the composition of the passing gas after elevating the temperature was changed to the one comprising 2.6% by volume of propylene, 8% by volume of oxygen, 15% by volume of water vapor and 74.4% by volume of nitrogen. As a result, a hot spot having a maximum temperature was observed at a site located 470 mm apart from the end of the raw material gas inlet side of a catalyst layer, wherein ΔT at the maximum temperature was 31° C. In addition, the rate of reaction of propylene was 98.6%, the selectivity factor of acrolein was 88.1%, the selectivity factor of acrylic acid was 5.8%, and the yield of acrolein and acrylic acid was 92.6%.

EXAMPLE 7

An oxidation reaction was carried out in a similar manner to that in Example 1, except that the time for passing the passing gas after elevating the temperature was changed to 1.5 hours. As a result, a hot spot having a maximum temperature was observed at a site located 470 mm apart from the end of the raw material gas inlet side of a catalyst layer, wherein ΔT at the maximum temperature was 31° C. In addition, the rate of reaction of propylene was 98.6%, the selectivity factor of acrolein was 88.1%, the selectivity factor of acrylic acid was 5.8%, and the yield of acrolein and acrylic acid was 92.6%.

COMPARATIVE EXAMPLE 7

An oxidation reaction was carried out in a similar manner to that in Example 1, except that the temperature of a heating medium bath was elevated to 310° C. without passing the passing gas through a catalyst layer after elevating the temperature, and except that thereafter a raw material gas was immediately passed through the catalyst layer. As a result, a hot spot having a maximum temperature was observed at a site located 400 mm apart from the end of the raw material gas inlet side of the catalyst layer, wherein ΔT at the maximum temperature was 41° C. In addition, the rate of reaction of propylene was 98.9%, the selectivity factor of acrolein was 86.5%, the selectivity factor of acrylic acid was 5.0%, and the yield of acrolein and acrylic acid was 90.5%.

COMPARATIVE EXAMPLE 8

An oxidation reaction was carried out in a similar manner to that in Example 1, except that the time for passing the passing gas after elevating the temperature was changed to ten minutes. As a result, a hot spot having a maximum temperature was observed at a site located 400 mm apart from the end of the raw material gas inlet side of the catalyst layer, wherein ΔT at the maximum temperature was 40° C. In addition, the rate of reaction of propylene was 98.7%, the selectivity factor of acrolein was 86.7%, the selectivity factor of acrylic acid was 5.1%, and the yield of acrolein and acrylic acid was 90.6%.

COMPARATIVE EXAMPLE 9

An oxidation reaction was carried out in a similar manner to that in Example 1, except that the composition of the passing gas after elevating the temperature was changed to the one comprising 4.5% by volume of propylene, 12% by volume of oxygen, 10% by volume of water vapor and 73.5% by volume of nitrogen. As a result, a hot spot having a maximum temperature was observed at a site located 400 mm apart from the end of the raw material gas inlet side of the catalyst layer, wherein ΔT at this maximum temperature was 41° C. In addition, the rate of reaction of propylene was 98.9%, the selectivity factor of acrolein was 86.5%, the selectivity factor of acrylic acid was 5.0%, and the yield of acrolein and acrylic acid was 90.5%.

COMPARATIVE EXAMPLE 10

An oxidation reaction was carried out in a similar manner to that in Example 1, except that the composition of the passing gas after elevating the temperature was changed to the one comprising 0.6% by volume of propylene, 8% by volume of oxygen, 15% by volume of water vapor and 76.4% by volume of nitrogen. As a result, a hot spot having a maximum temperature was observed at a site located 400 mm apart from the end of the raw material gas inlet side of the catalyst layer, wherein ΔT at this maximum temperature was 40° C. In addition, the rate of reaction of propylene was 98.7%, the selectivity factor of acrolein was 86.7%, the selectivity factor of acrylic acid was 5.1%, and the yield of acrolein and acrylic acid was 90.6%.

COMPARATIVE EXAMPLE 11

An oxidation reaction was carried out in a similar manner to that in Example 1, except that the composition of the gas as passed when the temperature of a heating medium bath was elevated to 310° C. was changed to the one comprising 2% by volume of propylene, 8% by volume of oxygen, 15% by volume of water vapor and 75% by volume of nitrogen. As a result, a hot spot having a maximum temperature was observed at a site located 550 mm apart from the end of the raw material gas inlet side of a catalyst layer, wherein ΔT at this maximum temperature was 20° C. In addition, the rate of reaction of propylene was 94.7%, the selectivity factor of acrolein was 88.0%, the selectivity factor of acrylic acid was 5.6%, and the yield of acrolein and acrylic acid was 88.6%. From the results, it is considered that the catalyst was poisoned when the temperature thereof was elevated, because ΔT at the hot spot was decreased as compared to the one in Example 1 while the rate of reaction of propylene also was decreased.

EXAMPLE 8

To 1000 parts of water, 500 parts of ammonium paramolybdate, 12.3 parts of ammonium paratungstate and 1.4 parts of potassium nitrate were added, heated and agitated, and thereafter a solution in which 4.1 parts of 85% by mass phosphoric acid is dissolved in 100 parts of water was added thereto, and further heated and agitated (Liquid C). Aside from this, to 850 parts of water, 50 parts of nitric acid of 60% by mass were added and homogenized, and then 114.5 parts of bismuth nitrate were added thereto and dissolved. To the mixture, 143.0 parts of ferric nitrate, 309.0 parts of cobalt nitrate, 7.0 parts of zinc nitrate, 3.2 parts of silver nitrate and 6.1 parts of magnesium nitrate were sequentially added and dissolved (Liquid D). Liquid D was added to Liquid C to form a slurry, and then heated and agitated, so that most of water was evaporated. The resultant caked matter was dried at a temperature of 130° C., and then calcined at a temperature of 300° C. in an atmosphere of air for a period of one hour, and pulverized. To 100 parts of the resultant pulverized product, 2 parts of graphite were added and mixed, which were then formed into rings having an outer diameter of 4 mm, an inner diameter of 2 mm and a length of 4 mm by using a tablet forming machine. This formed tablet product was calcined at a temperature of 500° C. in an atmosphere of air for a period of six hours, whereby Catalyst 2 was obtained. The elementary composition of Catalyst 2 comprised $Mo_{12}W_{0.2}Bi_1Fe_{1.5}P_{0.15}Ag_{0.08}Co_{4.5}Zn_{0.1}Mg_{0.1}K_{0.06}$, as an atomic ratio except oxygen.

The temperature of a heating medium bath of a tubular type of fixed bed steel reactor having an inner diameter of 25.4 mm as provided with the heating medium bath was set to a temperature of 180° C., and the inlet side for raw material gas was filled with a mixture of 620 ml of Catalyst 2 and 130 ml of a spherical alumina having an outer diameter of 5 mm, while the outlet side was filled with 750 ml of Catalyst 2, wherein the length of a catalyst layer was 3005 mm.

The heating medium bath temperature was elevated to a temperature of 310° C. at a rate of 50° C./hour, while a gas comprising 9% by volume of oxygen, 10% by volume of water vapor and 81% by volume of nitrogen was passed through this catalyst layer at a space velocity of 240 $hour^{-1}$.

Then, with the heating medium bath temperature maintained at a temperature of 310° C., a gas comprising 2% by volume of propylene, 8% by volume of oxygen, 15% by volume of water vapor and 75% by volume of nitrogen was passed through the catalyst layer at a space velocity of 1000 $hour^{-1}$ for a period of three hours.

Subsequently, with the heating medium bath temperature maintained at a temperature of 310° C., a raw material gas comprising 5% by volume of propylene, 12% by volume of oxygen, 10% by volume of water vapor and 73% by volume of nitrogen was passed through the catalyst layer at a reaction temperature (i. e., a heating medium bath temperature) of 310° C. at a space velocity of 1000 $hours^{-1}$. When the temperatures of the catalyst layer were measured at this time, a hot spot having a maximum temperature was observed at a site located 550 mm apart from the end of the inlet side for the raw material gas, wherein ΔT at the maximum temperature was 32° C. In addition, the rate of reaction of propylene was 99.0%, the selectivity factor of acrolein was 89.0%, the selectivity factor of acrylic acid was 6.2%, and the yield of acrolein and acrylic acid was 94.2%.

COMPARATIVE EXAMPLE 12

An oxidation reaction was carried out in a similar manner to that in Example 4, except that the temperature of a heating medium bath was elevated to 310° C. without passing the passing gas after elevating the temperature, and except that thereafter a raw material gas was immediately passed through the catalyst layer. As a result, a hot spot having a maximum temperature was observed at a site located 450 mm apart from the end of the raw material gas inlet side of the catalyst layer, wherein ΔT at the maximum temperature was 44° C. In addition, the rate of reaction of propylene was 99.4%, the selectivity factor of acrolein was 86.5%, the selectivity factor of acrylic acid was 5.9%, and the yield of acrolein and acrylic acid was 91.8%.

INDUSTRIAL APPLICABILITY

According to the method for producing methacrolein and/or methacrylic acid by subjecting isobutylene and/or tertiary butanol to a vapor-phase catalytic oxidation with molecular oxygen in the presence of a solid oxidation catalyst in a tubular type of fixed bed reactor, of the present invention, a temperature of a hot-spot zone can be sufficiently controlled, whereby methacrolein and methacrylic acid can be produced with a high yield.

Furthermore, the use of the compound oxide represented by the above-mentioned formula (1) as the solid oxidation catalyst further enhances the yield of methacrolein and methacrylic acid.

According to the method for producing acrolein and/or acrylic acid by subjecting propylene to a vapor-phase catalytic oxidation with molecular oxygen in the presence of a solid oxidation catalyst in a tubular type of fixed bed reactor, of the present invention, a temperature of a hot-spot zone can be sufficiently controlled, whereby acrolein and acrylic acid can be produced with a high yield.

Furthermore, the use of the compound oxide represented by the above-mentioned formula (2) as the solid oxidation catalyst further enhances the yield of acrolein and acrylic acid.

The invention claimed is:

1. A method for producing methacrolein and/or methacrylic acid by passing a raw material gas comprising isobutylene and/or tertiary butanol and oxygen through a catalyst layer in a tubular type of fixed bed reactor which is filled with a solid oxidation catalyst, which comprises passing a gas comprising isobutylene and/or tertiary butanol in a concentration lower than that of said raw material gas, and oxygen through said catalyst layer for a period of one hour or more prior to passing said raw material gas through said catalyst layer.

2. A method for producing methacrolein and/or methacrylic acid, which comprises:
   filling a tubular type of fixed bed reactor with a solid oxidation catalyst;
   elevating a temperature of the resultant catalyst layer to a range of 250° C. to 400° C. while passing a gas including oxygen, nitrogen, water vapor and 0 to 0.5% by volume of isobutylene and/or tertiary butanol through said catalyst layer;
   passing a gas including 1 to 3.8% by volume of isobutylene and/or tertiary butanol, 7 to 16% by volume of oxygen and 5 to 50% by volume of water vapor through said catalyst layer at a temperature of 250° C. to 400° C. for a period of one hour or more; and thereafter
   passing a raw material gas including 4 to 9% by volume of isobutylene and/or tertiary butanol, 7 to 16% by volume of oxygen and 5 to 50% by volume of water vapor through said catalyst layer at a temperature of 250° C. to 400° C.

3. The method for producing methacrolein and/or methacrylic acid according to claim 1 or 2, wherein said solid oxidation catalyst is a compound oxide represented by the following formula (1):

$$Mo_aBi_bFe_cA_dX_eY_fZ_gO_h \tag{1}$$

wherein Mo, Bi, Fe and O represent molybdenum, bismuth, iron and oxygen, respectively; A represents nickel and/or cobalt; X represents at least one element selected from the group consisting of magnesium, zinc, chromium, manganese, tin and lead; Y represents at least one element selected from the group consisting of phosphorus, boron, sulfur, tellurium, silicon, germanium, cerium, niobium, titanium, zirconium, tungsten and antimony; Z represents at least one element selected from the group consisting of potassium, sodium, rubidium, cesium and thallium; and each of a, b, c, d, e, f, g and h represents an atomic ratio of each element, wherein $0.1 \leq b \leq 5$, $0.1 \leq c \leq 5$, $1 \leq d \leq 12$, $0 \leq e \leq 10$, $0 \leq f \leq 10$ and $0.01 \leq g \leq 3$ when a=12, and h means an atomic ratio of oxygen necessary to satisfy the atomic valence of each of said elements.

4. A method for producing acrolein and/or acrylic acid by passing a raw material gas comprising propylene and oxygen through a catalyst layer in a tubular type of fixed bed reactor which is filled with a solid oxidation catalyst, which comprises passing a gas comprising propylene in a concentration lower than that of said raw material gas, and oxygen through said catalyst layer for a period of one hour or more prior to passing said raw material gas through said catalyst layer.

5. A method for producing acrolein and/or acrylic acid, which comprises:
   filling a tubular type of fixed bed reactor with a solid oxidation catalyst;
   elevating a temperature of the resultant catalyst layer to a range of 250° C. to 400° C. while passing a gas including oxygen, nitrogen, water vapor and 0 to 0.5% by volume of propylene through said catalyst layer;
   passing a gas including 1 to 3.8% by volume of propylene, 7 to 16% by volume of oxygen and 5 to 50% by volume of water vapor through said catalyst layer at a temperature of 250° C. to 400° C. for a period of one hour or more; and thereafter
   passing a raw material gas including 4 to 9% by volume of propylene, 7 to 16% by volume of oxygen and 5 to 50% by volume of water vapor through said catalyst layer at a temperature of 250° C. to 400° C.

6. The method for producing acrolein and/or acrylic acid according to claim 4 or 5, wherein said solid oxidation catalyst is a compound oxide represented by the following formula (2):

$$Mo_{a'}Bi_{b'}Fe_{c'}A'_{d'}X'_{e'}Y'_{f'}Z'_{g'}Si_{h'}O_i \tag{2}$$

wherein Mo, Bi, Fe, Si and O represent molybdenum, bismuth, iron, silicon and oxygen, respectively; A' represents nickel and/or cobalt; X' represents at least one element selected from the group consisting of magnesium, zinc, chromium, manganese, tin, strontium, barium, copper, silver and lead; Y' represents at least one element selected from the group consisting of phosphorus, boron, sulfur, tellurium, aluminum, gallium, germanium, indium, lanthanum, cerium, niobium, tantalum, titanium, zirconium, tungsten and antimony; Z' represents at least one element selected from the group consisting of potassium, sodium, rubidium, cesium and thallium; each of a', b', c', d', e', f', g', h' and i represents an atomic ratio of each element, wherein $0.01 \leq b' \leq 5$, $0.01 \leq c' \leq 5$, $1 \leq d' \leq 12$, $0 \leq e' \leq 10$, $0 \leq f' \leq 10$, $0.001 \leq g' \leq 3$ and $0 \leq h' \leq 20$ when a'=12, and i means an atomic ratio of oxygen necessary to satisfy the atomic valence of each of said elements.

* * * * *